US008740750B2

(12) United States Patent
Jerichow

(10) Patent No.: US 8,740,750 B2
(45) Date of Patent: Jun. 3, 2014

(54) DEVICE AND METHOD FOR CONTROLLING AND/OR REGULATING A TRAINING AND/OR REHABILITATION UNIT

(76) Inventor: Ulrich Jerichow, Gelnhausen (DE)

( * ) Notice: Subject to any disclaimer, the term of this patent is extended or adjusted under 35 U.S.C. 154(b) by 1060 days.

(21) Appl. No.: 12/673,968

(22) PCT Filed: Jul. 24, 2008

(86) PCT No.: PCT/EP2008/059737
§ 371 (c)(1),
(2), (4) Date: Jan. 21, 2011

(87) PCT Pub. No.: WO2009/024427
PCT Pub. Date: Feb. 26, 2009

(65) Prior Publication Data
US 2011/0105281 A1    May 5, 2011

(30) Foreign Application Priority Data
Aug. 18, 2007  (DE) .......................... 10 2007 039 124

(51) Int. Cl.
*A63B 21/00*    (2006.01)
(52) U.S. Cl.
USPC ............ 482/4; 482/8; 482/9; 482/51; 482/54; 600/529; 600/531; 600/533; 600/532; 455/410; 455/411; 455/502
(58) Field of Classification Search
USPC ........... 482/8, 4, 9, 51, 54; 455/410, 411, 502
See application file for complete search history.

(56) References Cited

U.S. PATENT DOCUMENTS

| | | |
|---|---|---|
| 4,463,764 A | 8/1984 | Anderson |
| 6,387,053 B1 | 5/2002 | Pessenhofer |
| 6,450,922 B1 | 9/2002 | Henderson |
| 6,921,369 B1 | 7/2005 | Gehrke |
| 7,122,632 B2 | 10/2006 | Foster |
| 7,387,780 B2 | 6/2008 | Foster |

(Continued)

FOREIGN PATENT DOCUMENTS

| | | |
|---|---|---|
| AT | 407 950 B | 7/2001 |
| DE | 6 912 241 U | 8/1969 |

(Continued)

OTHER PUBLICATIONS

Baumann, R. et al., "Solid State Electrolyte Sensors for the Determination of Oxygen, Carbon Dioxide, and Total Flow Rates Associated to Respiration in Human Subjects," Executive Summary to the ESTEC Contract No. 15450/01/ NL/JS, Oct. 13, 2006, 10 pages.

(Continued)

*Primary Examiner* — Jerome W Donnelly
(74) *Attorney, Agent, or Firm* — Christensen O'Connor Johnson Kindness PLLC

(57) ABSTRACT

In at least one embodiment, a device for controlling and/or regulating a training and/or rehabilitation unit comprises a training and/or rehabilitation unit, a sensor unit having sensors for determining oxygen concentration and for determining carbon dioxide concentration, a control unit for the sensors, a microcontroller in the control unit for controlling the heating power of heating elements of the sensors, depending on breath flow volume, for maintaining constant sensor temperatures, and a resistance and/or braking arrangement of the training and/or rehabilitation unit that can be controlled and/or regulated based on a breathing gas composition determined by the sensor unit. The device can be used to increase endurance, preferably by way of altitude training.

42 Claims, 3 Drawing Sheets

(56) References Cited

U.S. PATENT DOCUMENTS

| | | |
|---|---|---|
| 7,585,948 B2 | 9/2009 | Foster |
| 2003/0013072 A1 | 1/2003 | Thomas |
| 2005/0003475 A1 | 1/2005 | Foster |
| 2006/0201507 A1 | 9/2006 | Breen |
| 2006/0263850 A1 | 11/2006 | Foster |
| 2006/0263851 A1 | 11/2006 | Foster |
| 2010/0002001 A1 | 1/2010 | Jerichow |

FOREIGN PATENT DOCUMENTS

| | | |
|---|---|---|
| DE | 199 53 866 A1 | 6/2001 |
| DE | 100 08 969 A1 | 9/2001 |
| DE | 20 2004 007 273 U1 | 7/2004 |
| DE | 697 29 202 T2 | 5/2005 |
| DE | 20 2006 011 058 U1 | 10/2006 |
| EP | 0 176 277 A3 | 4/1986 |
| EP | 0 861 419 B1 | 9/1998 |
| EP | 1 055 393 A3 | 11/2000 |
| EP | 1 139 099 A2 | 10/2001 |
| EP | 1 825 888 A1 | 8/2007 |

OTHER PUBLICATIONS

International Search Report mailed Nov. 6, 2008, issued in corresponding International Application No. PCT/EP2008/059737, filed Jul. 24, 2008, 2 pages.

West, A.R., "Basic Solid State Chemistry," 2d ed., John Wiley & sons, Ltd, Chichester, England, 1999, Chap. 7.5, "Ionic Conductivity," pp. 321-361.

DEVICE AND METHOD FOR CONTROLLING AND/OR REGULATING A TRAINING AND/OR REHABILITATION UNIT

FIELD

The present disclosure relates to a device and a method for controlling and/or regulating a training and/or rehabilitation unit.

BACKGROUND

It is known that altitude training can be implemented in order to improve physical performance, for example, of a sportsperson. Here, a corresponding training effect is achieved by longer training periods in high mountain regions. A precise regulation and control of the increase in performance is however not possible with altitude training of this type.

For a precise examination of the lung function, the spirometry method can be used. Thus for example, in DE 6 912 241 U1, a spirometry breathing mask is described for examining the lung function, in particular during physical effort. Furthermore, according to U.S. Pre-Grant Publication No. 2006/0201507, a spirometry device for measuring oxygen intake can be used. With systems of this type, it is however not possible to monitor the oxygen and carbon dioxide composition of the inspired air and the expired air at the same time.

In order to make stamina training with simultaneous monitoring of the performance data and body functions more comfortable for a sportsperson, an integration of the training device into a system for providing virtual reality is possible. According to DE 20 2004 007 273 U1, a relaxation and/or experience device, in particular a spa installation, with a film presentation by means of a film projector device and a film display area within closed rooms, wherein this contains movement, sound, wind, odor, light and/or other radiation generation devices and/or sensor devices that are connected with each other via a control device, the activities and functionalities of which are adjusted to events in the film presentation in terms of time, place, and/or in their intensities. Here, with systems of this type and similar systems, no recording and analysis is made however of the bodily functions such as lung function, so that it is also not possible to control the effect or success of the application. Furthermore, with systems of this type, no specific fitness or training programs and no medical applications can be implemented.

DESCRIPTION OF THE DRAWINGS

Many of the aspects and the attendant advantages of this disclosure will become more readily appreciated as the same become better understood by reference to the following detailed description, when taken in conjunction with the accompanying drawings, wherein.

DETAILED DESCRIPTION

The present disclosure provides a system with which a person can complete specific fitness or rehabilitation programs, for example, wherein a training and/or rehabilitation unit used for the purpose can be controlled and/or regulated depending on the breathing gas composition of the user.

Figure 1:
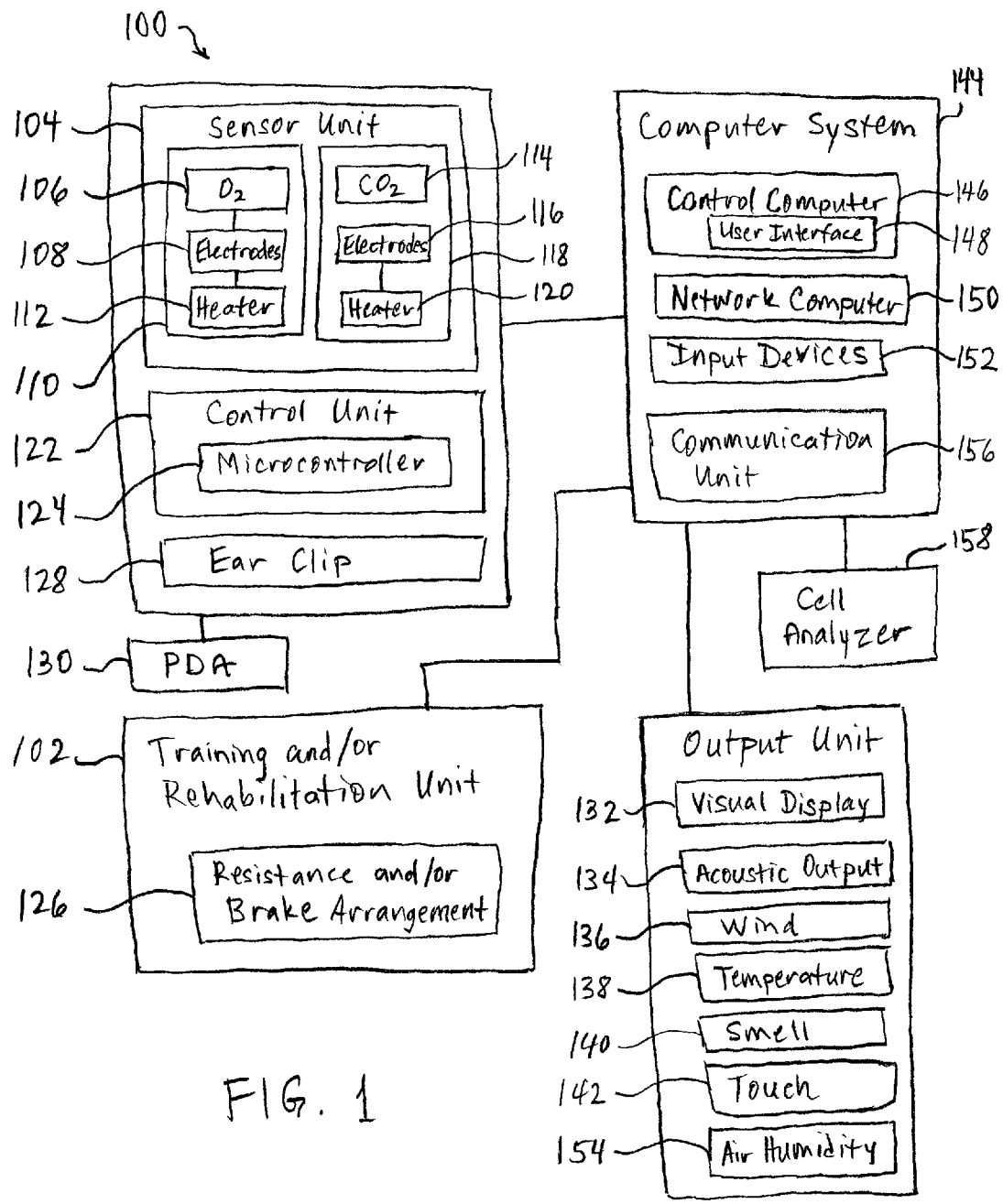
FIG. 1 is a block diagram illustrating aspects of equipment and systems usable according to the present disclosure.

Referring to FIG. 1, disclosed herein are embodiments of a device 100 for controlling and/or regulating a training and/or rehabilitation unit, wherein, in at least one embodiment, the device comprises at least:

one training and/or rehabilitation unit 102;

one sensor unit 104 with a heatable electrochemical solid state electrolyte sensor 106, which in order to determine the oxygen concentration contains yttrium contaminated zirconium oxide as an electrolyte, two electrodes 108 and a support element 110, and a heating element 112, and in order to determine the carbon dioxide concentration contains a further heatable electrochemical solid state electrolyte sensor 114, which comprises a super-fast sodium ion conductor as an electrolyte, two electrodes 116 and a support element 118 and a heating element 120;

one control unit for the sensors 122;

one microcontroller 124 in the control unit for the control, which is dependent on the flow volume of the breathing, of the heating power of heating elements of the sensors for the purpose of maintaining constant sensor temperatures; and one controllable and/or adjustable resistance and/or brake arrangement 126 of the training and/or rehabilitation unit, which depends on the breathing gas composition determined by the sensor unit.

A decisive advantage of such a device 100 results from the possibility that the training and/or rehabilitation unit 102 can be controlled and/or regulated with the aid of a controllable and/or adjustable resistance and/or brake arrangement 126, either separately or in such a manner that it is assignable for the oxygen and/or carbon dioxide concentration determined for the inspired and expired air, as well as the breathing flow volume. In other words, a required parameter of the breathing gas composition of the user can be achieved by means of the fact that with the aid of the controllable and/or adjustable resistance and/or brake arrangement 126, the training load of the user can be changed accordingly. A further advantage arises from the fact that with a training procedure, the lung function of a person using the device 100 can be precisely monitored. Furthermore, an undersupply of oxygen can be detected immediately, for example, and the training can be modified accordingly. Additionally, complex calibration as is required with spirometry devices is no longer necessary.

Figure 2:
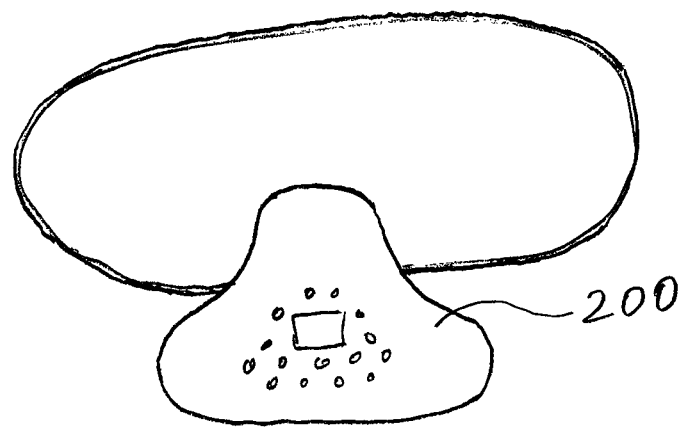
FIG. 2 depicts a mask with a sensor.

With an advantageous embodiment variant, the sensor unit 104 is arranged directly in a component through which the inspired and expired air of the person flows. Thus, the sensor unit can, for example, be incorporated into a breathing mask 200 (see FIG. 2) that the person wears. This arrangement has the particular advantage that an extremely low dead volume is present.

According to the one or more embodiments, an oxygen sensor 106 is used that for the selective conduction of oxygen ions, contains yttrium-contaminated zirconium oxide as an electrolyte between two electrodes 108, and a support element 110, a heating element 112, as well as a carbon dioxide sensor 114 that contains an electrolyte from a super-fast sodium ion conductor, two electrodes 116, a support element 118, and a heating element 120 (1). The aforementioned super-fast sodium ion conductor, also known as NASICON, can be described by the formula $Na_{3-x}Zr_2(PO_4)_{1+x}(SiO_4)_{2-x}$ (2). Sensors of this type have the advantage that they can be produced to be particularly small and light, and in a cost-efficient manner. Thus, for sensors of this type, for example, dimensions of 20×3.5×0.5 mm can be achieved (1). Such miniaturized sensors are thus particularly suitable for installation into a breathing mask 200.

For the measurement of the oxygen concentration in the blood, it is advantageous when an ear clip is integrated into the device. Additionally, the device can contain an ear clip 128 for measuring the pulse of the user. With the device, comprehensive performance data can thus be determined, and further medical parameters of the user, such as heart rate, can be recorded. The measurement data obtained, can in an advantageous manner, be recorded with the aid of a connected Personal Digital Assistant (PDA) 130.

The training and/or rehabilitation unit 102 can, for example, be an ergometer, a fitness machine, a cross trainer, a rowing machine ergometer, a rowing machine, a treadmill, a walking machine, spin bike, or bicycle. The resistance and/or brake arrangement 126 of the training and/or rehabilitation unit can, for example, contain a pneumatic, hydraulic, mechanical, or electro-magnetic brake, an eddy-current brake, or band brake. A training and/or rehabilitation unit 102 can thus, for example, comprise a frame, a means for absorbing the force, such as pedals, a drive transmission system, a rotation element, and a resistance and/or brake arrangement. Here, in particular, magnetic or electric eddy-current brakes have the advantage that they can be actuated in a simple manner and are less prone to wear and tear.

Furthermore, the device can comprise, with an advantageous embodiment, means for two- and three-dimensional visual display 132, at least one acoustic output 134 and/or recording device and means for generating wind 136, temperatures 138, and/or odors 140. Furthermore, the device can contain means for stimulating the sense of touch 142. Furthermore, it is advantageous when the components of the training and/or rehabilitation unit 102, including the controllable and/or adjustable resistance and/or brake arrangement 126, the sensor unit 104 and the control unit 122 for the sensors, are connected with each other via a computer system 144, and are thus controlled and/or read by such a computer system. Here, the computer system 144 can consist at least of a control computer 146 with a user interface 148.

With an advantageous embodiment variant of the device, a network computer 150 is connected to the control computer 146 in order to calculate the image for the right and left eye. The signals generated during this process can be forwarded to a helmet 300 with LCDs 310, which is worn on the head of the user in order to generate a virtual environment (Head Mounted Display (HMD)). Alternatively, the signals generated can also be used for stereo production in order to generate a three-dimensional display on a screen. It is furthermore advantageous when the control computer 146 is connected with one or more input devices 152 with at least six degrees of freedom in order to determine the position and orientation, and the input devices are selectively equipped with one or more buttons. It is furthermore advantageous that, for example, isometric, isotonic, and/or elastic input devices 152 are connected to the control computer 146, wherein with said input devices, recording of the movement of the direction of vision, body movement or head movement, and/or a position determination can be conducted.

With a further advantageous embodiment, with the input devices 152, gestures, facial expressions, and/or language can be recorded. Thus, a combination of physical and psychological stimuli is made possible, and the use of an aroma or altitude training can be conducted in a virtual, three-dimensional environment.

Figure 3:
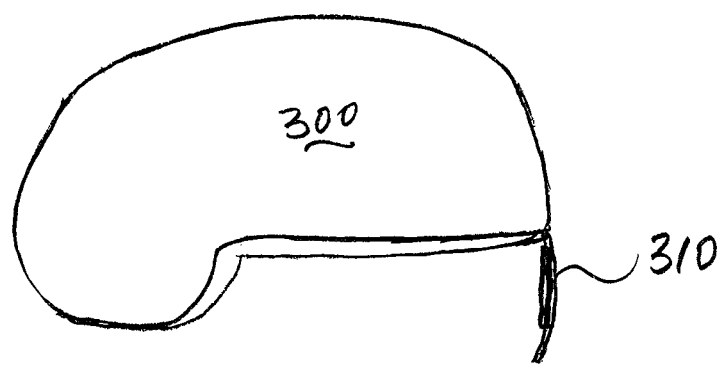
FIG. 3 depicts a helmet with an LCD display.

In a particularly advantageous embodiment variant, a Head Tracker is used, for example, as an input device, which can also be affixed to the helmet 300 (see FIG. 3) with LCDs 310, which is worn on the head of the user in order to generate the virtual environment (Head Mounted Display (HMD)). Furthermore, it is advantageous that the visual display unit 132 shows a non-moving image, a moving or non-moving object, a computer graphic, and/or two- and/or three-dimensional moving images or films. For this purpose, conventional monitors can also be used for the two-dimensional display.

With an advantageous embodiment, the visual display unit 132 can show an image with a viewing angle of between 0° and 179°, or when the system is used in the fitness, spa, or medical field, it can also show an image with a viewing angle of 180° or more than 180°, wherein moving and/or non-moving real images photographed previously by the user can also be shown.

The acoustic output unit 134 can, for example, reproduce musical instruments, human voices, ambient sounds such as animal noises, wind, rain, waterfalls, thunder, and/or noises made by vehicle engines, shots, pumps, explosions, and/or earthworks. It is particularly advantageous when wind 136, temperature 138, odor 140, and/or air humidity 154 can be adapted to the situation shown in the virtual reality.

Furthermore, it is advantageous when via a communication unit 156, instructions and/or information can be passed on to the user of the device, and the user can make contact via a communication unit 156 with a person starting the device 100. With an advantageous further development of the system, more precise blood count analyses can be conducted before, during, and/or after use by means of the removal of blood. For example, with the aid of a cell analysis device 158 that is connected to the computer system 144, preferably a device for flow cytometry, the composition of the blood cells can be precisely determined. Additionally, when a specific antibody is used, preferably coupled with a florescent dye, an analysis of surface markers on cells is possible.

Figure 4:
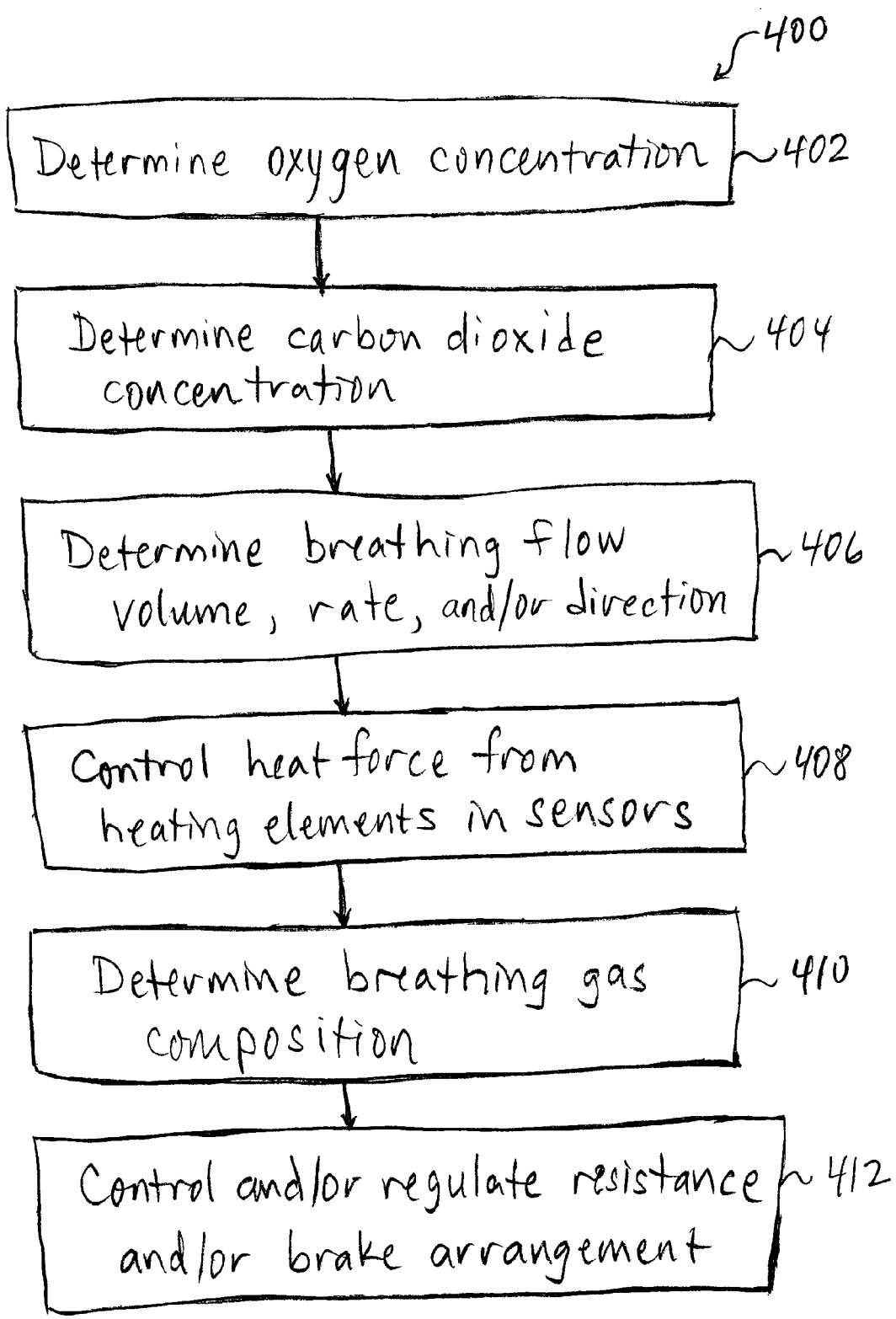
FIG. 4 is a flow diagram of a method according to the present disclosure.

Also in the spirit of present disclosure are methods for controlling and/or regulating a training unit and/or a rehabilitation unit, wherein, in at least one embodiment 400 shown in FIG. 4:

a person uses a training unit and/or rehabilitation unit;
  in a sensor unit, an oxygen concentration determination is conducted 402 with the aid of a heatable, electrochemical, solid state electrolyte sensor 106, and a carbon dioxide concentration determination is conducted 404 with the aid of a further heatable, electrochemical, solid state electrolyte sensor 114;
  a control of the heating power from heating elements 112, 120 in the sensors, which depends on the breathing flow volume of the person 406, is conducted 408 with the aid of a microcontroller 124 in order to maintain constant sensor temperatures; and
  depending on the breathing gas composition determined 410 by the sensor unit and/or the determined breathing flow volume of the person, a resistance or brake arrangement of the training and/or rehabilitation unit is controlled and/or regulated 412.

The foregoing method 400 can be implemented using the device described above in one or more of the aforementioned embodiments. In a particularly advantageous manner, the determination of the oxygen concentration of the air breathed is conducted 402 by measuring the flow that travels under constant voltage through the electrolyte of the oxygen sensor from the cathode to the anode, wherein a linear connection exists between the resulting electric current and the concentration of oxygen. Furthermore, it is advantageous when the carbon dioxide concentration is determined 404 by means of a logarithmic connection between the voltage between the electrodes of the carbon dioxide sensor and the carbon dioxide concentration. Furthermore, it is advantageous that the breathing flow volume is determined 406 with the heating power of the heating elements of the sensors that are controlled 408 by the microcontroller, which is necessary in order to maintain a constant sensor temperature.

The determination of the overall flow rate of the air breathed can be conducted 406 with the sensor element, using thin layer anemometry. Furthermore, the flow direction of the breathing gas can be determined 406 either by using the measured oxygen and/or carbon dioxide concentration gradients or the temperature profile on the sensor 104. The method 400 disclosed herein has the advantage that at the same time, the volume flow, flow direction and thus the oxygen and carbon dioxide composition of the inspired air and expired air can be monitored with a breath-by-breath resolution. The oxygen and carbon dioxide concentrations can therefore be clearly assigned to the inspired air and expired air. Here, it is particularly advantageous when, depending on the determined breathing gas composition 410 of a person using the training and/or rehabilitation unit 102, with the aid of the controllable and/or adjustable resistance and/or brake arrangement 126, the training load of the person can be changed according to requirements. Thus, depending on the determined oxygen and/or carbon dioxide content of the breathing gas 410, with the aid of the controllable and/or adjustable resistance and/or brake arrangement 126, the training load of the person can be adapted as needed. For example, the oxygen and/or carbon dioxide content of the expired air can be reduced by increasing the load with the aid of the resistance and/or brake arrangement.

Thus, the device can be used to increase the stamina performance, preferably by means of simulated altitude training.

Thus, for example, a reduction in the oxygen content of the expired air from 17% to 12% can be achieved by a corresponding increase in the training load.

Furthermore, by individually adapting the load, the ratio (respiratory quotient) between inspired and expired air can be maintained at a constant for every training or therapy program by means of the device according to the disclosure, regardless of the condition on the day or in training.

Furthermore, it is advantageous that a computer program with program code is used for implementing all the aforementioned method stages when the program is implemented in a computer. Here, it is advantageous when the computer program is stored on a support device that can be read by a machine, with a program code for conducting all the aforementioned method stages.

When the device 100 and/or the method 400 according to the present disclosure is used, professional and competitive sportspeople can prepare in an optimum manner for forthcoming competitions with altitude training units in a virtual, realistic environment. To a greater extent, the realistic training under low-oxygen conditions is aimed towards increasing the personal performance and individual fitness of hobby and amateur sportspeople. Here specifically, the costly and time-intensive flights and accommodation in high mountain regions can be avoided. Furthermore, training, which is essentially more efficient, is possible since the system is available 24 hours a day and easy to access in logistical terms.

In the field of rehabilitation and the spa sector, this system could, for example, combine an aroma treatment with passive altitude training and oxygen therapy in a virtual, three-dimensional environment. In such an environment, a combination of this nature of relaxation and improvement of personal performance and strengthening of the immune system can be achieved.

In the medical field, the system can be used for an aroma treatment, altitude training and/or oxygen therapy in a three-dimensional environment, wherein the four senses—sight, touch, smell and hearing—are stimulated. Due to the mobilization of the body's own immune system that is achieved as a result, an application with people suffering from diseases such as cancer, allergies, and metabolic disorders is possible.

Furthermore, the three-dimensional display technology in particular offers an opportunity to positively influence the progression of specific psychological disorders, such as fear, and with auto-immune system disorders due to the effect of images and sounds.

REFERENCES (1) R. Baumann[1,2], S. Fasoulas[1], M. Gläser[1], C. Gritzner[1], F. Hammer[2], J. Heisig[1], R. Kahle[1], T. Kirschke[1], T. Schmiel[1], M. Völkel[2]. Solid State Electrolyte Sensors for the Determination of Oxygen, Carbon Dioxide, and Total Flow Rates Associated to Respiration in Human Subjects. [1]Institute for Aerospace Engineering, Technische Universitat Dresden, 01062 Dresden, Germany. [2]ESCUBE GmbH, Nobelstr. 15, 70569 Stuttgart, Germany (PRO2-FR-Exec-Sum-05-02-10 Executive Summary to the ESTEC Contract No. 15450/01/NL/JS CCN 1+2).
(2) West, A. R., Grundlagen der Festkorperchemie, Verlage Chemie, Weinheim (1992).

While illustrative embodiments have been illustrated and described, it will be appreciated that various changes can be made therein without departing from the spirit and scope of the disclosure.

The invention claimed is:

1. A device for controlling and/or regulating a training and/or rehabilitation unit, wherein the device comprises:
    a training and/or rehabilitation unit;
    a sensor unit with a heatable electrochemical solid-state electrolyte sensor, which in order to determine the oxygen concentration, contains yttrium-contaminated zirconium oxide as an electrolyte, two electrodes, a support element, and a heating element, and in order to determine the carbon dioxide concentration, contains a further heatable electrochemical solid-state electrolyte sensor, which comprises a sodium ion conductor as an electrolyte, two electrodes, and a support element and a heating element;
    a control unit for the sensors;
    a microcontroller in the control unit configured to control a heating power of the heating elements of the sensors and maintain constant sensor temperatures, wherein the heating power is controlled dependent on a flow volume of breathing of a person; and
    a controllable and/or adjustable resistance and/or brake arrangement of the training and/or rehabilitation unit that depends on a breathing gas composition determined by the sensor unit.

2. The device according to claim 1, wherein the sensor unit is arranged directly in a component through which inspired and expired air of the person flows.

3. The device according to claim 1, wherein the sensor unit is arranged in a breathing mask.

4. The device according to claim 1, further comprising an integrated ear clip for measuring oxygen concentration in the person's blood.

5. The device according to claim 1, further comprising an integrated ear clip for measuring the person's pulse.

6. The device according to claim 1, further comprising a data storage for storing performance data with further medical parameters of the person.

7. The device according to claim 1, wherein data measured by the sensor unit is recorded with the aid of a connected personal digital assistant.

8. The device according to claim 1, wherein the training and/or rehabilitation unit is an ergometer, fitness machine, cross trainer, rowing ergometer machine, rowing machine, treadmill, walking machine, spin bike, or bicycle.

9. The device according to claim 1, wherein the resistance and/or brake arrangement of the training and/or rehabilitation unit contains a pneumatic, hydraulic, mechanical or electromagnetic brake, an eddy-current brake, or band brake.

10. The device according to claim 1, further comprising a two- and/or three-dimensional visual display, at least one acoustic output and/or recording device, and an output unit configured to generate wind, temperatures, and/or odors.

11. The device according to claim 1, further comprising an output unit configured to stimulate the sense of touch.

12. The device according to claim 1, wherein components of the training and/or rehabilitation unit, including the controllable and/or adjustable resistance and/or brake arrangement, the sensor unit, and the control unit for the sensors are connected with each other via a computer system.

13. The device according to claim 12, wherein the computer system contains at least one control computer with a user interface.

14. The device according to claim 13, wherein a network computer is connected to the control computer in order to calculate an image for the person's right and left eye.

15. The device according to claim 1, wherein the device is configured to forward signals to a helmet with LCDs that is worn on the head of the person in order to generate a virtual environment in a head mounted display.

16. The device according to claim 15, wherein the signals are usable for stereo production in order to generate a three-dimensional display on a screen.

17. The device according to claim 13, wherein the control computer is connected with one or more input devices with at least six degrees of freedom in order to determine the position and orientation of the person, and wherein the input devices are selectively equipped with one or more buttons.

18. The device according to claim 17, wherein isometric, isotonic, and/or elastic input devices are connected to the control computer.

19. The device according to claim 17, wherein with the input devices, recording of the movement of the direction of vision, body movement, or head movement, and/or a position determination is conducted.

20. The device according to claim 17, wherein with the input devices, gestures, facial expressions, and/or language can be recorded.

21. The device according to claim 17, wherein a head tracker is used as an input device.

22. The device according to claim 1, further comprising a visual display unit that shows a non-moving image, a moving or non-moving object, a computer graphic, and/or two- or three-dimensional moving images or films.

23. The device according to claim 22, wherein the visual display unit shows an image with a viewing angle of between 0° and 179°.

24. The device according to claim 22, wherein, when the visual display unit is used in the fitness, spa, or medical field, it can show an image with a viewing angle of 180° or more than 180°.

25. The device according to claim 22, wherein the visual display unit shows moving and/or non-moving images photographed by the user.

26. The device according to claim 1, further comprising an acoustic output unit that reproduces musical instruments, human voices, ambient sounds, such as animal noises, wind, rain, waterfalls, thunder, and/or noises made by vehicle engines, shots, pumps, explosions, and/or earthworks.

27. The device according to claim 1, further comprising an output unit configured to adapt wind, temperature, odor, and/or air humidity according to a situation shown in virtual reality.

28. The device according to claim 1, further comprising a communication unit from which instructions and/or information can be passed on to the person.

29. The device according to claim 1, wherein the communication unit is configured to allow the person to make contact with another person operating the device.

30. The device according to claim 12, further comprising a cell analysis device connected to the computer system.

31. A method for controlling and/or regulating a training and/or rehabilitation unit being used by a person, the method comprising:
determining, in a sensor unit, an oxygen concentration with the aid of a heatable, electrochemical, solid-state electrolyte sensor, which in order to determine the oxygen concentration, contains yttrium-contaminated zirconium oxide as an electrolyte between two electrodes, together with a support element and a heating element;
determining, in the sensor unit, a carbon dioxide concentration with the aid of a further heatable, electrochemical, solid-state electrolyte sensor, which contains a sodium ion conductor as an electrolyte, two electrodes, a support element, and a heating element;
controlling a heat power from the heating elements in the sensors, which depends on a breathing flow volume of the person, with the aid of a microcontroller in a sensor control unit in order to maintain constant sensor temperatures; and
depending on a breathing gas composition determined by the sensor unit and/or the breathing flow volume of the person, controlling and/or regulating a resistance or brake arrangement of the training and/or rehabilitation unit.

32. The method according to claim 31, wherein the oxygen concentration of air breathed by the person is determined by measuring a current flow that travels under constant voltage through the electrolyte between the electrodes of the oxygen sensor, wherein a linear connection exists between the resulting electric current and the concentration of oxygen.

33. The method according to claim 31, wherein the carbon dioxide concentration is determined by a logarithmic connection between a voltage between the electrodes of the carbon dioxide sensor and the carbon dioxide concentration.

34. The method according to claim 31, wherein the breathing flow volume is used to determine the heating power of the heating elements of the sensors that are controlled by the microcontroller and that maintain a constant sensor temperature.

35. The method according to claim 31, further comprising using thin layer anemometry in the sensor unit to determine the overall flow rate of air breathed by the person.

36. The method according to claim 31, further comprising determining a flow direction of the breathing gas either by using measured oxygen and/or carbon dioxide concentration gradients or a temperature profile on the sensors.

37. The method according to claim 31, further comprising monitoring, at the same time, the volume flow, flow direction, and oxygen and carbon dioxide composition of the inspired air and expired air with a breath-by-breath resolution.

38. The method according to claim 31, wherein depending on the determined breathing gas composition of the person using the training and/or rehabilitation unit, with the aid of the controllable and/or adjustable resistance and/or brake arrangement, changing the training load of the person.

39. The method according to claim 38, wherein depending on the determined oxygen and/or carbon dioxide content of the breathing gas, with the aid of the controllable and/or adjustable resistance and/or brake arrangement, adapting the training load of the person.

40. The method according to claim 39, wherein the oxygen and/or carbon dioxide content of expired air is reduced by increasing the training load of the person with the aid of the resistance and/or brake arrangement.

41. A non-transitory, computer-readable storage medium having executable instructions stored thereon that, in response to execution by a computer, cause the computer to conduct the method stages according to claim 31, wherein the instructions are implemented with the support of the computer.

42. The non-transitory, computer-readable storage medium according to claim 41, wherein the instructions cause the computer to change a training load of the person depending on the determined breathing gas composition of the person using the training and/or rehabilitation unit, with the aid of the controllable and/or adjustable resistance and/or brake arrangement.

\* \* \* \* \*